(12) United States Patent
Bonrath et al.

(10) Patent No.: US 9,790,164 B2
(45) Date of Patent: Oct. 17, 2017

(54) PROCESS OF PRODUCTION OF DEHYDROLINALYL ACETATE (II)

(71) Applicant: DSM IP ASSETS B.V., Heerlen (NL)

(72) Inventors: Werner Bonrath, Basel (CH); Fabrice Aquino, Basel (CH); Johannes Tschumi, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 8 days.

(21) Appl. No.: 14/889,561

(22) PCT Filed: May 7, 2014

(86) PCT No.: PCT/EP2014/059376
§ 371 (c)(1),
(2) Date: Nov. 6, 2015

(87) PCT Pub. No.: WO2014/180921
PCT Pub. Date: Nov. 13, 2014

(65) Prior Publication Data
US 2016/0122277 A1    May 5, 2016

(30) Foreign Application Priority Data

May 8, 2013  (EP) .................... 13166963

(51) Int. Cl.
*C07C 67/02*    (2006.01)
*C07C 67/08*    (2006.01)

(52) U.S. Cl.
CPC .................... *C07C 67/08* (2013.01)

(58) Field of Classification Search
USPC .............................. 560/261; 3/261
See application file for complete search history.

(56) References Cited

U.S. PATENT DOCUMENTS 7,355,066 B1 *  4/2008  Johnson ................ C07C 67/08
                                                  560/239

FOREIGN PATENT DOCUMENTS

WO    WO 2011/086135    7/2011

OTHER PUBLICATIONS

International Search Report for PCT/EP2014/059376, mailed Aug. 18, 2014, 2 pages.

* cited by examiner

*Primary Examiner* — Clinton Brooks
*Assistant Examiner* — Ana Z Muresan
(74) *Attorney, Agent, or Firm* — Nixon & Vanderhye P.C.

(57) ABSTRACT

The present invention is related to a novel and improved process for the production of dehydrolinalyl acetate (DLA), which IUPAC name is acetic acid 1-ethynyl-1,5-dimethyl-hex-4-enyl ester, starting from dehydrolinalool (DLL), which IUPAC name is 3,7-dimethyloct-6-en-1-yn-3-ol, by acetylation.

4 Claims, No Drawings

PROCESS OF PRODUCTION OF DEHYDROLINALYL ACETATE (II)

This application is the U.S. national phase of International Application No. PCT/EP2014/059376 filed 7 May 2014, which designated the U.S. and claims priority to EP Patent Application No. 13166963.2 filed 8 May 2013, the entire contents of each of which are hereby incorporated by reference.

The present invention is related to a novel and improved process for the production of dehydrolinalyl acetate (DLA), which IUPAC name is acetic acid 1-ethynyl-1,5-dimethyl-hex-4-enyl ester, starting from dehydrolinalool (DLL), which IUPAC name is 3,7-dimethyloct-6-en-1-yn-3-ol, by acetylation.

Dehydrolinalyl acetate (compound of formula (I))

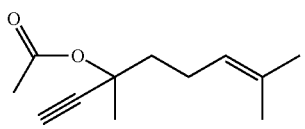

is an important and valuable compound for the use in the field of flavour and fragrance applications.

DLA can also be used in the production of linalylacetate (compound of formula (IV))

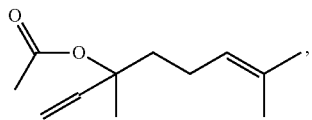

which is also an important and valuable compound for the use in the field of flavour and fragrance applications.

Nowadays, DLA is usually produced by an acetylation of DLL by using p-toluene sulfonic acid as an "organic-soluble" acid catalyst.

In course of this reaction significant amounts of side products, such as D,L-iso-3,7-dimethyl-7-octen-1-in-3-yl acetate (iso-DLA; compound of formula (V)),

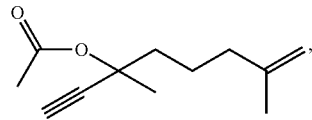

2,2,6-trimethyl-6-ethynyltetrahydropyrane (ETTP; compound of formula (VI))

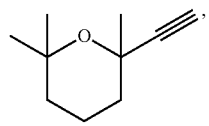

and 3-isopropenyl-1-methyl-2-methylene-cyclopentylacetate (compound of formula (VI))

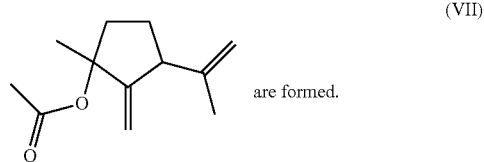

are formed.

The goal of the present invention was to find an improved process for the production of DLA, without the above mentioned disadvantages of the process of the prior art (especially reducing the amount of the side products).

Surprisingly it was found that in the absence of any catalyst, DLA is obtained by the acetylation of DLL with a significantly lower amount of undesired side products and with excellent selectivity and yield.

Therefore the present invention is related to the process of production of DLA, which is the compound of formula (I)

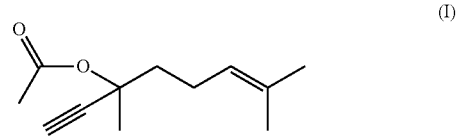

by reacting DLL, which is the compound of formula (II)

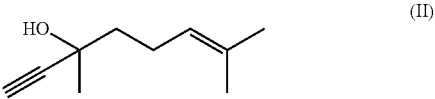

with acetic anhydride, which is the compound of formula (III)

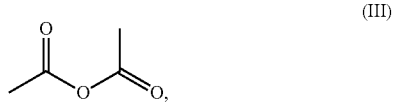

characterized in that the process is carried out in the absence of any catalyst.

The process according to the present invention is usually carried out at elevated temperatures.

Preferably the process according to the present invention is carried out at a temperature of more than 50° C., preferably more than 80° C., more preferably more than 100° C.

The process according to the present invention is preferably carried out at temperature of 100° C. to 160° C.

The process according to the present invention is usually carried out at normal pressure.

DLL and acetic anhydride ($Ac_2O$) can be added to the reaction mixture in equimolar amounts. It is also possible to use slight excess of either one of the compounds. Usually the acetic anhydride is used in an excess in regard to DLL. Preferably acetic anhydride (compound of formula (III)) is added in a ratio of 1:1 up to 8:1 (in regard to compound of formula (II)). More preferably acetic anhydride (compound of formula (III)) is added in a ratio of 1.1:1 up to 5:1 (in regard to compound of formula (II)).

The process according to the present invention is usually carried out without any solvent. But it would also be possible to use an inert solvent (or mixture of inert solvents).

Preferably the process according to the present invention is carried out without any solvents.

The starting material (compound of formula (II) and compound of formula (III)) can be mixed together before the process is started or one of the starting material can be added to the other while the process is going on.

Usually the compound of formula (II) is put into the reaction vessel and then the compound of formula (III) is added during a period of time.

After the addition and mixture of all the starting material the reaction mixture is let reacted for some time.

Usually the reaction time for the process according to the present invention is between 2 to 20 hours, preferably 2-18 hours, more preferably 2-15 hours.

At the end of the reaction, the remaining acetate anhydride and the acetic acid (product of the process) is removed from the reaction solution. This is usually done by distillation (normal pressure or at a reduced pressure).

The DLA which is obtained by the process according to the present invention can be used as such (flavour and fragrance applications) or it can be used in the production of other useful compounds, especially linanylacetate (obtained by hydrogenation of DLA).

The following examples serve to illustrate the invention. If not otherwise stated all parts are given are related to the weight and the temperature is given in ° C.

EXAMPLES

Example 1

Into a 350 ml four necked round bottomed flask fitted with a thermometer and a reflux condenser 164.3 g DLL (1.06 mol) and 150 ml (1.6 mol) $Ac_2O$ were added under stirring.

The yellowish reaction solution was heated to 110° C. (internal temperature). After 14 h. Afterwards the $Ac_2O$ and AcOH-mixture was distilled at 10 mbar at 90-100° C.

DLA was obtained in a yield of 70%.

The same reaction was repeated with an amount of 250 ml $Ac_2O$ (reaction time 5 hours) and with an amount of 500 ml $Ac_2O$ (reaction time 5 hours).

DLA was obtained in a yield 90% (250 ml $Ac_2O$) and 94.2% (500 ml $Ac_2O$).

The invention claimed is:

1. A process for the production of dehydrolinalyl acetate (DLA) which is a compound of formula (I):

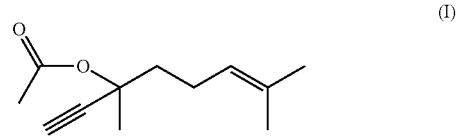

wherein the process comprises reacting dehydrolinalool (DLL) which is a compound of formula (II):

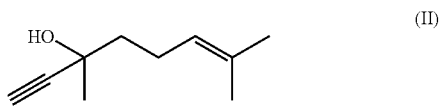

in a reaction solution with acetic anhydride which is a compound of formula (III):

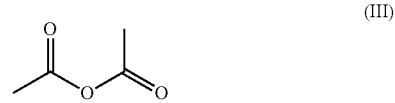

at a ratio of the compound of formula (III) to the compound of formula (II) of 1.5:1 up to 5:1, wherein the process is carried out in the absence of any catalyst at normal pressure and a temperature of 100-160° C. for 2 to 20 hours to yield DLA in an amount of 70% or greater.

2. The process according to claim 1, wherein the process is carried out in the absence of solvent.

3. The process according to claim 1, wherein the process forms acetic acid as a by-product of the reaction of the compound of formula (II) and the compound of formula (III), and wherein the process further comprises a step of removing any remaining acetate anhydride and acetic acid from the reaction solution.

4. The process according to claim 1, wherein the process yields of DLA in an amount of 90% or greater.

* * * * *